(12) United States Patent
Robert et al.

(10) Patent No.: US 8,767,510 B2
(45) Date of Patent: Jul. 1, 2014

(54) METHOD FOR CONTROLLING TRANSDUCERS OF AN ULTRASONIC PROBE, CORRESPONDING COMPUTER PROGRAM AND ULTRASONIC PROBE DEVICE

(75) Inventors: Sebastien Robert, Saint-Ouen (FR); Oliver Casula, Longpont sur Orge (FR); Arnaud Nadim, Chatenay Malabry (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 13/806,526

(22) PCT Filed: Jul. 25, 2011

(86) PCT No.: PCT/FR2011/051789
§ 371 (c)(1),
(2), (4) Date: Dec. 21, 2012

(87) PCT Pub. No.: WO2012/022886
PCT Pub. Date: Feb. 23, 2012

(65) Prior Publication Data
US 2013/0094328 A1    Apr. 18, 2013

(30) Foreign Application Priority Data
Jul. 28, 2010 (FR) .................... 10 56217

(51) Int. Cl.
*G01N 29/26*    (2006.01)
(52) U.S. Cl.
USPC ........................................ 367/95
(58) Field of Classification Search
USPC ................... 367/87, 103, 105, 95
See application file for complete search history.

(56) References Cited

U.S. PATENT DOCUMENTS

| 7,516,664 | B2 | 4/2009 | Meier et al. |
| 7,581,444 | B2 * | 9/2009 | Maurer et al. ............ 73/597 |
| 2006/0195273 | A1 | 8/2006 | Maurer et al. |
| 2009/0211361 | A1 | 8/2009 | Young et al. |

FOREIGN PATENT DOCUMENTS

WO    WO 2012022886    *    2/2012    ............. G01N 29/26

OTHER PUBLICATIONS

Prada, C., et al, "The iterative time reveral process: Analysis of the convergence," The Journal of the Acoustical Society of America, vol. 97, No. 1, pp. 62-71, (Jan. 1, 1995).
International Search Report Issued Nov. 17, 2011 in PCT/FR11/51789 Filed Jul. 25, 2011.
B. Beardsley, et al., "A Simple Scheme for Self-Focusing of an Array," Journal of Nondestructive Evaluation, vol. 14, No. 4, pp. 169-179, 1995.

* cited by examiner

*Primary Examiner* — Daniel Pihulic
(74) *Attorney, Agent, or Firm* — Oblon, Spivak, McClelland, Maier & Neustadt, L.L.P.

(57) ABSTRACT

A method for controlling ultrasonic transducers of an ultrasonic probe for inspecting an object includes: iterated at least twice, receiving from the transducers new measurement signals; measuring echoes due to reflections of ultrasonic waves on the object, the ultrasonic waves having emission delays with respect to one another, the emission delays having been determined from initial emission delays and all complementary emission delays determined previously; determining new complementary emission delays from the new measurement signals; controlling the transducers so they emit ultrasonic waves to the object, the ultrasonic waves having emission delays with respect to one another, the emission delays having been determined from the initial emission delays and all the complementary emission delays determined previously.

10 Claims, 6 Drawing Sheets

Figure 1:
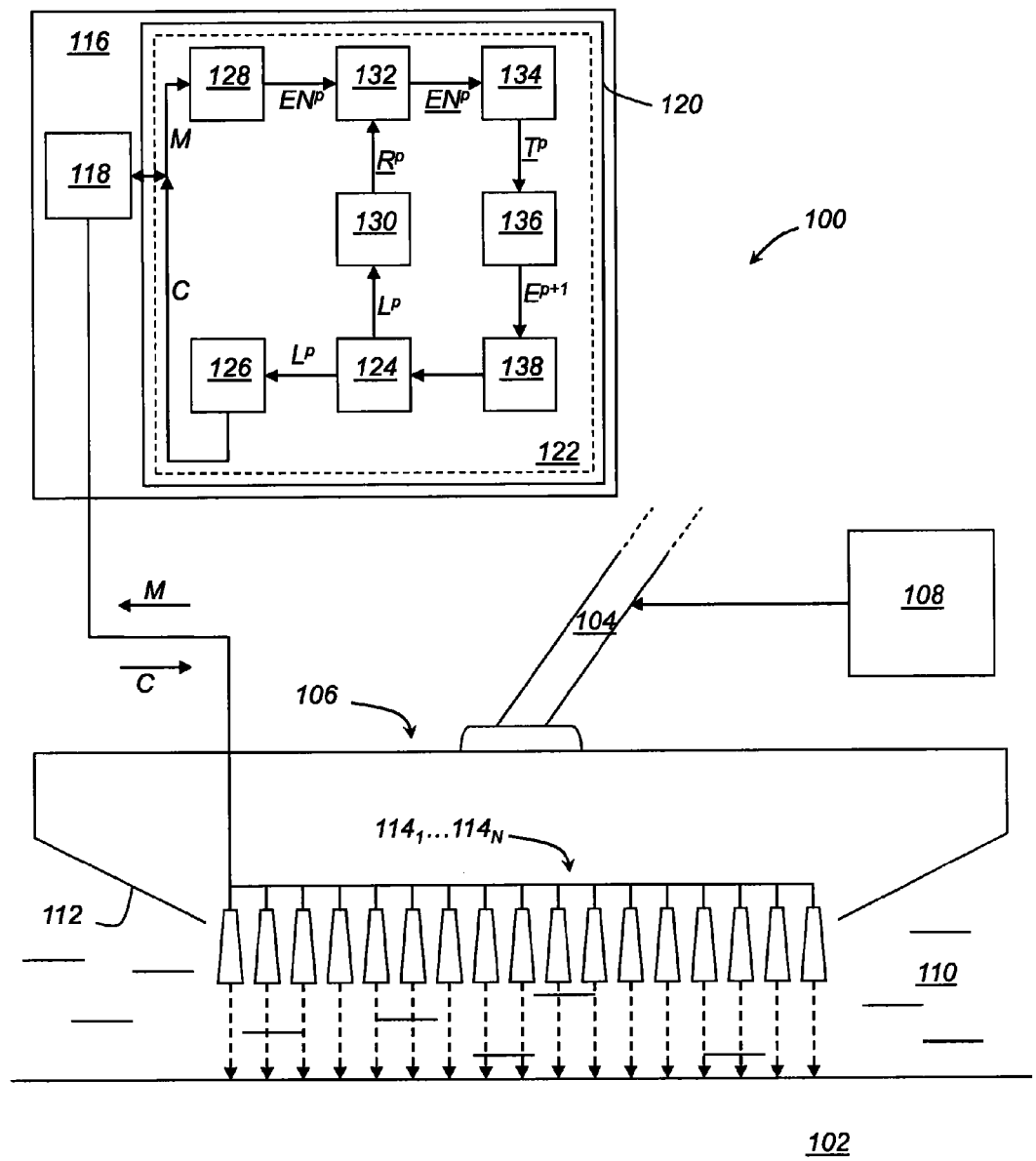

METHOD FOR CONTROLLING TRANSDUCERS OF AN ULTRASONIC PROBE, CORRESPONDING COMPUTER PROGRAM AND ULTRASONIC PROBE DEVICE

The present invention concerns a method for controlling transducers of an ultrasonic probe, a corresponding computer program and an ultrasonic inspection device.

The invention applies in particular to the field of the non-destructive testing of mechanical parts having a complex shape, in particular during immersion testing, in which a mechanical part is immersed in a liquid in order to be tested remotely, for example in the aeronautical sector. It may also apply to the medical field.

It concerns more precisely a method for controlling ultrasonic transducers of an ultrasonic probe for the purpose of testing an object, comprising the following steps:

controlling the transducers so that they emit towards the object ultrasound waves having initial emission delays $E^0$ with respect to one another, receiving from the transducers measurement signals $S^0$, measuring in particular echoes due to reflections of the ultrasound waves on the object, determining complementary emission delays $E^1$ from the measurement signals $S^0$, and controlling the transducers so that they emit towards the object ultrasound waves having emission delays $L^1$ with respect to one another, the emission delays $L^1$ having been determined from the initial emission delays $E^0$ and the complementary emission delays $E^1$.

A method that discloses these steps is known from the patent application published under the number US 2006/0195273.

More precisely, this document describes a method according to which the step of determining the complementary emission delays $E^1$ from the measurement signals $S^0$ consists of proceeding in two stages: first of all, an estimation of the contour of the object is calculated explicitly from the measurement signals $S^0$ obtained on the occasion of a first firing; then a delay law that can be assimilated to the complementary emission delays $E^1$ is calculated from this contour and applied on the occasion of a second firing.

More precisely also, in this document, the initial emission delays are zero delays. At the second firing, there are therefore not explicitly any emission delays $L^1$ determined from the initial emission delays $E^0$ and the complementary emission delays $E^1$, the delay law being directly established from the estimated contour of the object.

This method was developed for inspecting complex structures made from laminated composites, that is to say a matrix of organic resin reinforced with carbon fibre fabrics, and applies in particular to the detection of defects of the delamination type with an orientation almost parallel to the surface of the part. It makes it possible to form an incident wave front with the same curvature as the surface of the part, which minimises the distortion of the incident ultrasonic beam at the entry thereof into the part. The transmission of the beam in the part is thus optimised, which assists the detection of defects in the part compared with a non-adapted ultrasonic emission. The detection and location of defects takes place by analysis of the B-scan obtained (cumulative representation of the N measurement signals received by the N transducers of the probe). This method is particularly suited to laminated composite materials for which the folds have an orientation almost parallel to the surface and participate in fact in the degradation of the ultrasonic beam transmitted if the latter is not suited to the geometry of the object. In addition, this method is not restricted to this type of material; it may also be applied for inspecting other materials, in particular metal, with defects of the inclusion type.

Nevertheless, the use of this method for objects having a very complex geometry, that is to say among other things a surface very different from a substantially flat surface, provides a B-scan that cannot be used since it is still too noisy. In particular, when the surface of the object has locally a small radius of curvature compared with the dimensions of the probe, strong interferences between the waves reflected by the object remain and impair the representation of the B-scan.

It may thus be wished to improve the existing transducer control methods to allow inspection of objects with a very complex geometry.

The subject matter of the invention is therefore a method for controlling ultrasonic transducers of an ultrasonic probe for the purpose of inspecting an object, comprising the following steps:

controlling the transducers so that they emit towards the object ultrasound waves having initial emission delays $E^0$ with respect to one another, receiving from the transducers measurement signals $S^0$, measuring in particular echoes due to reflections of the ultrasound waves on the object, determining complementary emission delays $E^1$ from the measurement signals $S^0$, controlling the transducers so that they emit towards the object ultrasound waves having emission delays $L^1$ with respect to one another, the emission delays $L^1$ having been determined from the initial emission delays $E^0$ and the complementary emission delays $E^1$, and further comprising the following steps, iterated at least once, the iteration number being denoted p:

receiving from the transducers new measurement signals $S^p$, measuring echoes due to reflections of the ultrasound waves on the object, the ultrasound waves having emission delays $L^p$ with respect to one another, the emission delays $L^p$ having been determined from the initial emission delays $E^0$ and all the complementary emission delays $E^1 \ldots E^p$ determined previously, determining new complementary emission delays $E^{p+1}$ from the new measurement signals $S^p$, controlling the transducers so that they emit ultrasound waves towards the object, the ultrasound waves having emission delays $L^{p+1}$ with respect to one another, the emission delays $L^{p+1}$ having been determined from the initial emission delays $E^0$ and all the complementary emission delays $E^1 \ldots E^{p+1}$ determined previously.

Thus, by virtue of the invention, it is possible to determine emission delays enabling the ultrasound waves to reach the object to be inspected substantially simultaneously, and this in a few iterations only and whatever the complexity of the object.

Optionally, the step during which new complementary emission delays $E^{p+1}$ are determined from the new measurement signals $S^p$ comprises the following steps: determining round trip times $t^p$ from the new measurement signals $S^p$; determining the new complementary emission delays $E^{p+1}$ from the trip times $t^p$.

Optionally also, the step during which the round trip times $t^p$ are determined from the new measurement signals $S^p$ comprises, for each transducer, the following step: determining a reference instant on the new measurement signal $S_n^p$ supplied by the transducer in question, in particular the instant where the envelope of the amplitude of the new measurement signal $S_n^p$ takes a maximum value, n designating the index of the transducer in question.

Optionally also, the step during which the round trip times $t^p$ are determined from the new measurement signals $S^p$ comprises the following steps: determining reception offsets $R^p$ from the emission delays $L^p$; offsetting in time the new measurement signals $S^p$ according to the reception offsets $R^p$.

Optionally also, the step during which the new complementary emission delays $E^{p+1}$ are determined from the trip times $t^p$ comprises, for each transducer, the following step: determining the new complementary emission delay $E_n^{p+1}$ for the transducer in question according to the equation: $E_n^{p+1}=\frac{1}{2}[\max(t_1^p, \ldots, t_N^p)-t_n^p]$, where $t_n^p$ is the round trip time determined from the new measurement signal $S_n^p$ supplied by the transducer in question, n designating the index of the transducer in question and N the number of transducers.

Optionally also, the method further comprises the following step: at the end of each iteration p of the steps, evaluating a stop test which, if it is satisfied, stops the method, and which, if it is not satisfied, causes the execution of a new iteration p+1 of the steps.

Optionally also, the ultrasound waves emitted by the transducers are pulse waves having a pseudo time period T, and the stop test comprises the satisfaction of the following inequality:

$$\max(E_1^p, \ldots, E_N^p) \leq \frac{T}{4}.$$

Optionally also, the stop test comprises the check that the number of iterations has reached a predetermined number, for example three or four iterations.

Another subject matter of the invention is a computer program downloadable from a communication network and/or recorded on a medium that can be read by a computer and/or executable on a processor, comprising instructions for the execution of the steps of an inspection method according to the invention, when said program is executed on a computer.

Another subject matter of the invention is an ultrasonic inspection device comprising:
- a probe comprising a housing and ultrasonic transducers attached to the housing,
- control means designed to implement a method for controlling the transducers according to the invention.

Figure 2:
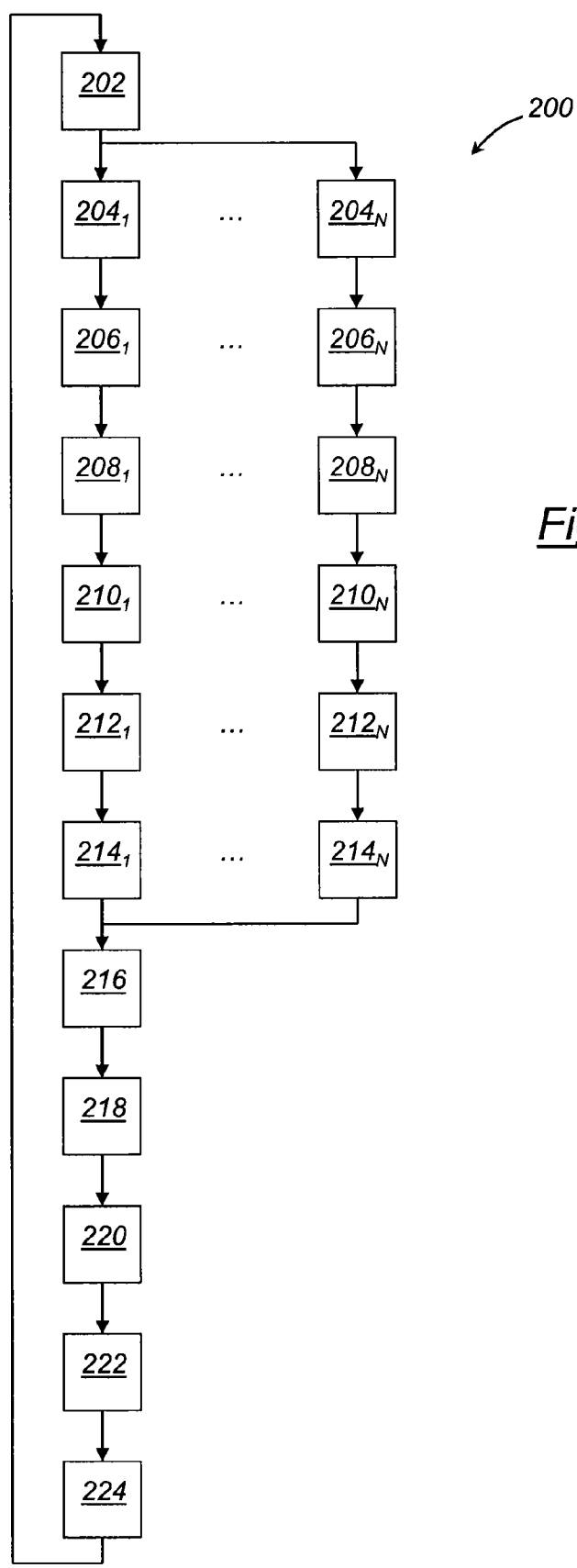
Figure 3:
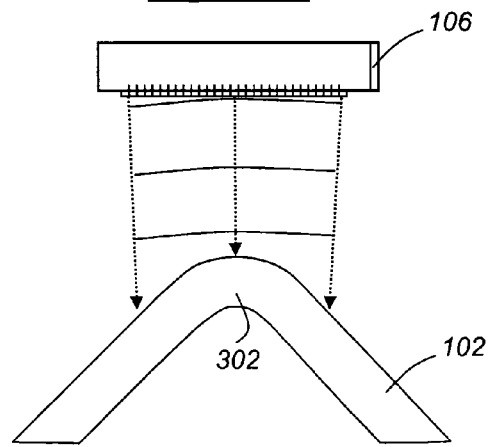
Figure 4:
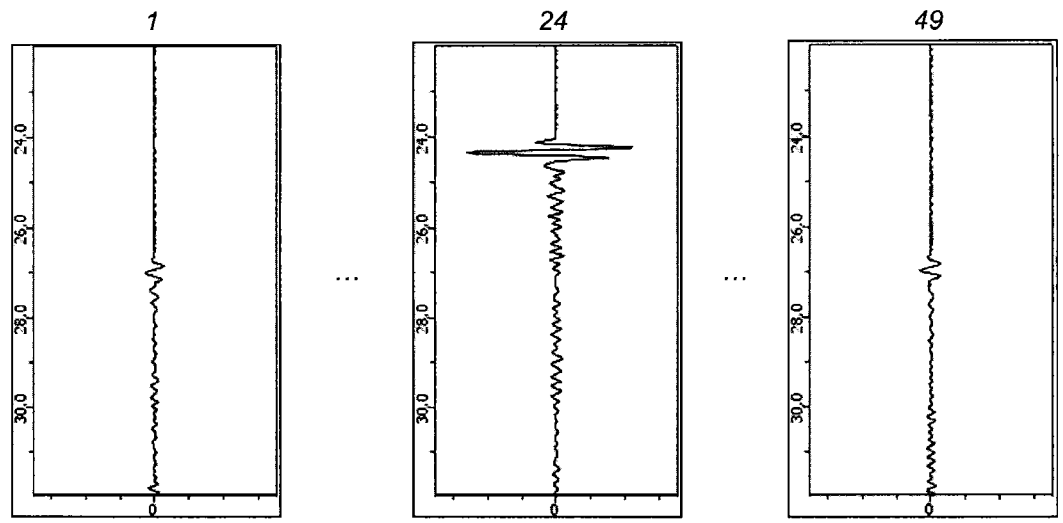
Figure 5:
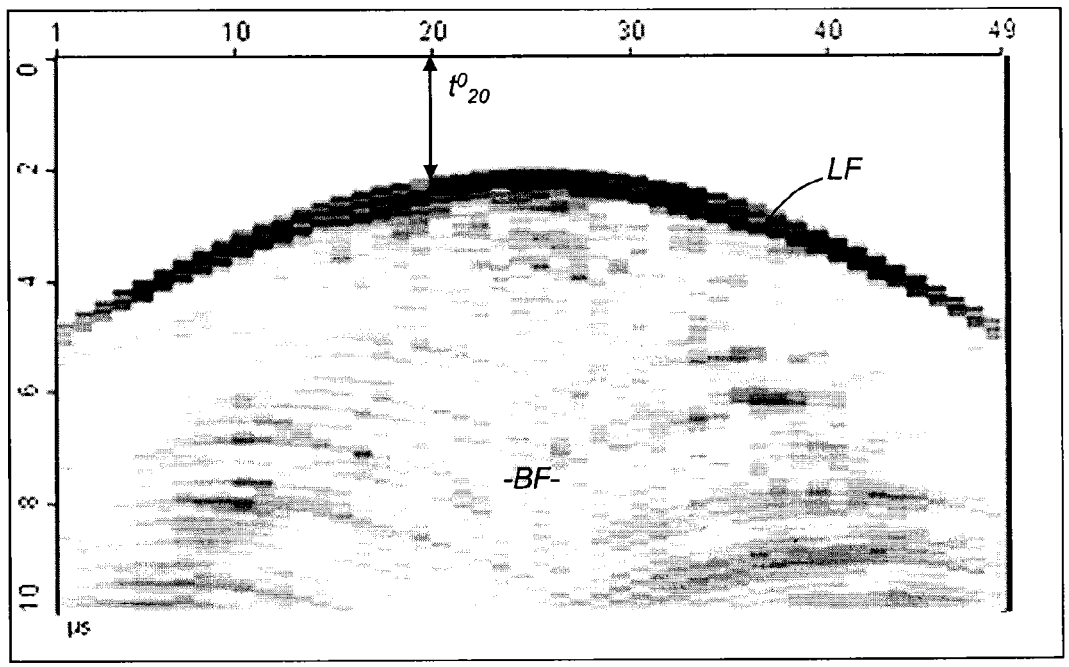
Figure 6:
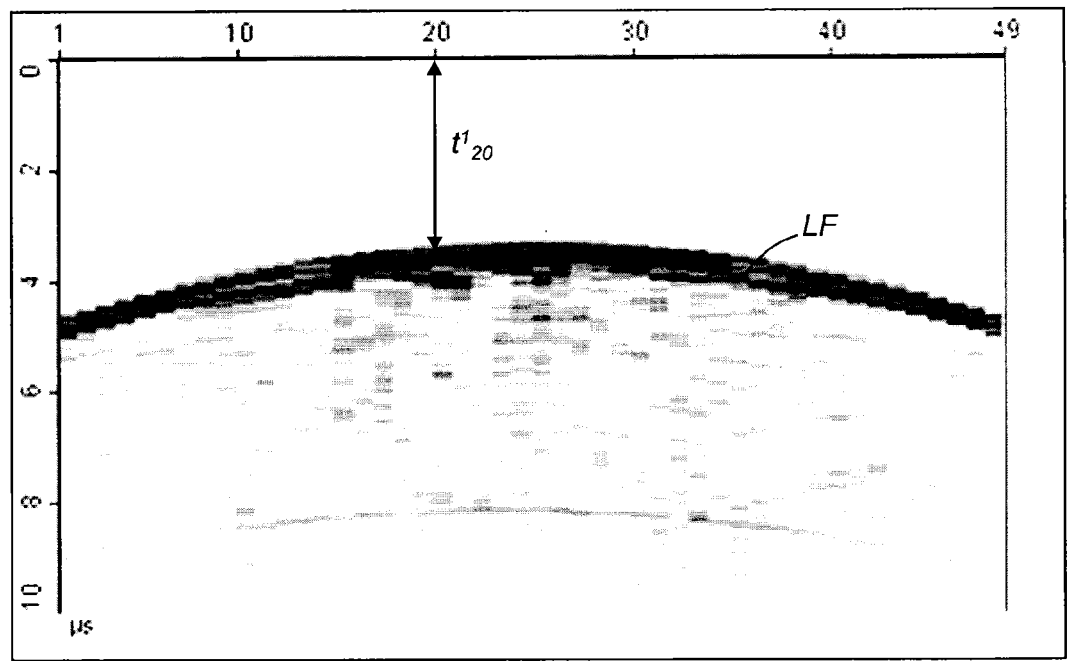
Figure 7:
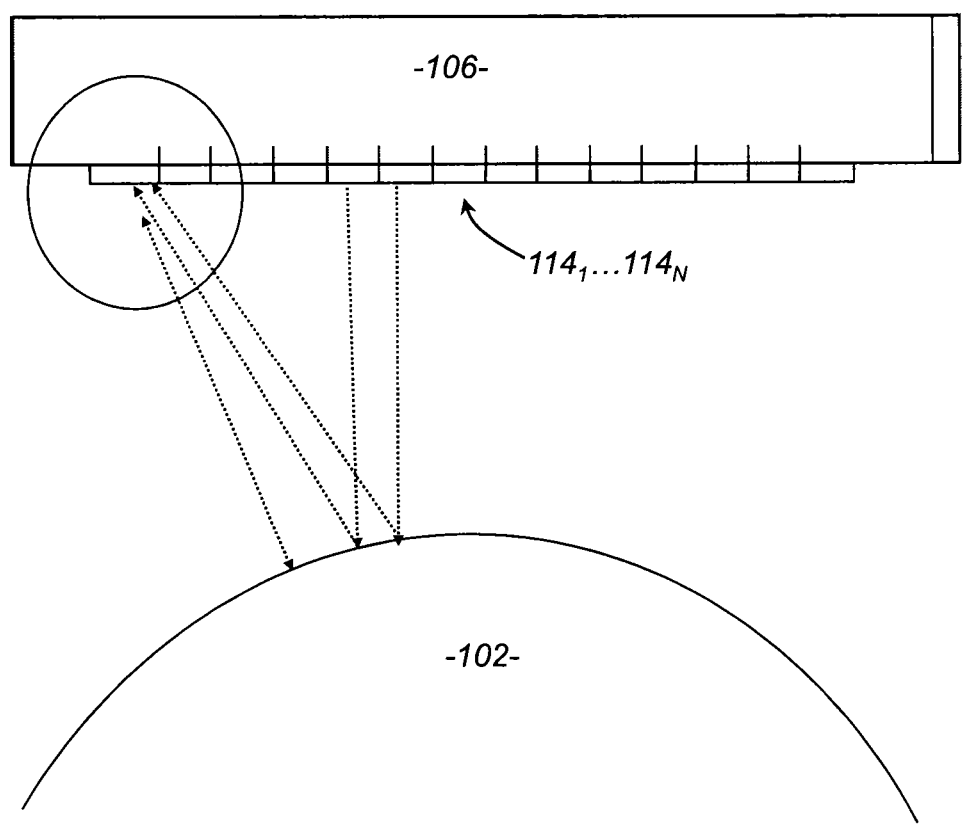
Figure 8:
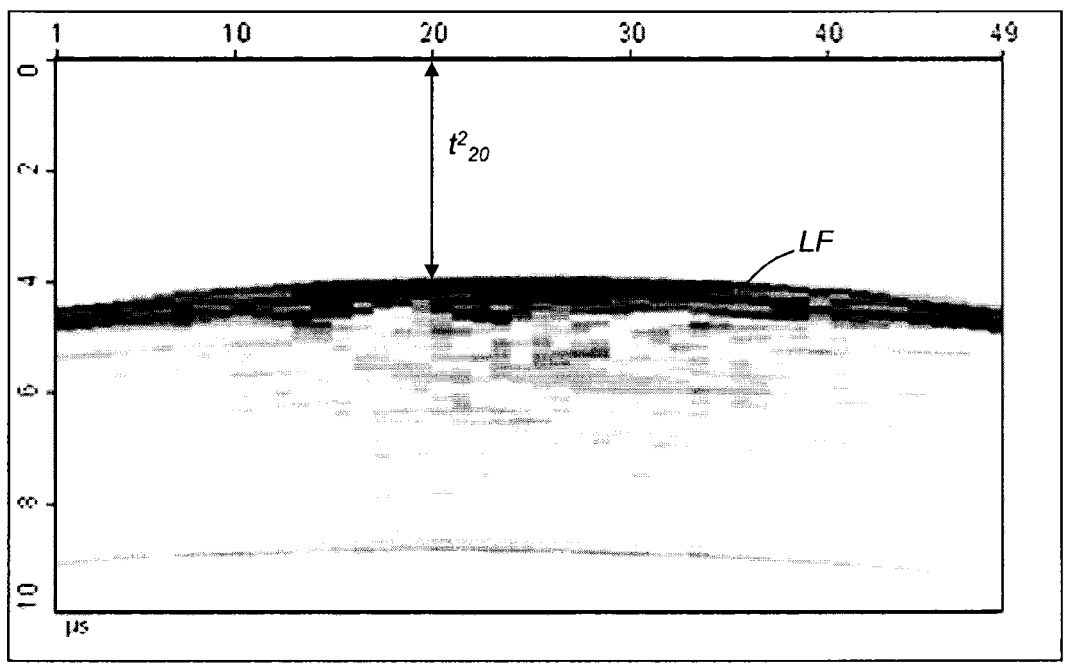
Figure 9:
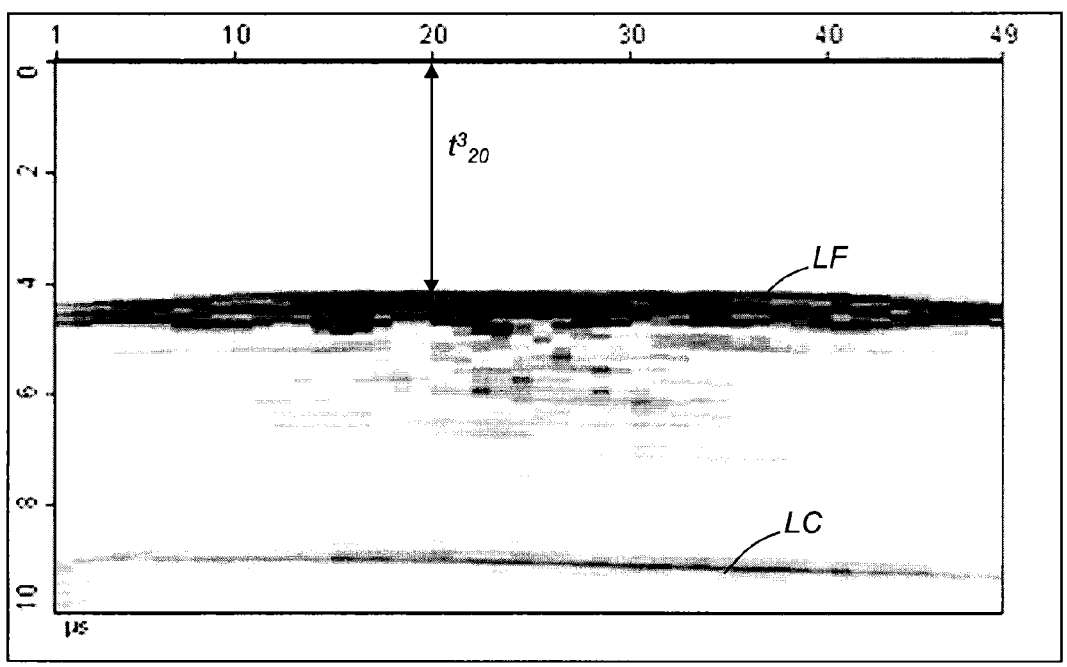

The invention will be better understood with the help of the following description, given solely by way of example and made with reference to the accompanying drawings, in which:

FIG. 1 shows schematically the general structure of an inspection device according to one embodiment of the invention, FIG. 2 illustrates the successive steps of an inspection method comprising a loop of steps and implemented by the inspection device of FIG. 1, FIG. 3 shows an example of use of the probe of FIG. 1 for inspecting an angled object, FIG. 4 shows the measurement signals supplied by transducers of the device of FIG. 1, FIGS. 5 and 6 are B-scans obtained from measurement signals, for respectively a first and second iteration of the loop of steps, FIG. 7 illustrates an interference phenomenon, and FIGS. 8 and 9 are B-scans obtained from measurement signals, for respectively a third and fourth iteration of the loop of steps.

With reference to FIG. 1, a device 100 for inspecting an object 102 according to one embodiment of the invention comprises an articulated arm 104, an ultrasonic probe 106 fixed to the articulated arm 104 and means 108 of controlling the articulated arm designed to control the articulated arm 104 so that the latter moves the probe 106 with respect to the object 102.

The object 102 is for example a mechanical part that it is wished to examine by non-destructive testing or, in a medical context, a part of the human body that it is wished to examine non-invasively.

In the embodiment in FIG. 1, the object 102 is immersed in a liquid, such as water 110, and the probe 106 is held at a distance from the object 102 so that the water 110 separates them.

The probe 106 comprises first of all a housing 112, that is to say a non-deformable structure element that serves as a reference frame attached to the probe 106.

The probe 106 further comprises N transducers $114_1 \ldots 114_N$ placed in the housing 112 and attached to the latter. The transducers $114_1 \ldots 114_N$ are designed to emit ultrasonic waves in the direction of the object 102 in response to control signals C, in principal directions parallel to one another, indicated by arrows in broken lines in FIG. 1.

The transducers $114_1 \ldots 114_N$ are further designed so as to detect echoes of the ultrasonic waves reflected on and in the object 102 and to supply measurement signals M corresponding to these echoes.

The inspection device 100 further comprises an electronic circuit 116 controlling the transducers $114_1 \ldots 114_N$ of the probe 106. The electronic circuit 116 is connected to the probe 106 in order to transmit the control signals C to it and in order to receive the measurement signals M. The electronic circuit 116 is for example that of a computer. The electronic circuit 116 has a central processing unit 118, such as a microprocessor that is designed to emit the control signals C to the probe 106 and to receive the measurement signals M from the probe 106, and a memory 120 in which a computer program 122 is recorded.

The computer program 122 comprises an instruction loop 124 to 138 able to be executed several times. In the remainder of the description, an iteration rank p will be used to distinguish the various iterations of the instruction loop 124 to 138. The initial execution of the loop corresponds to p equal to zero (first iteration), while each repetition of the loop corresponds to the value p:p is equal to one for the first repetition (that is to say the second iteration), to two for the second repetition (that is to say the third iteration), etc.

The computer program 122 comprises first of all instructions 124 designed to determine emission delays $L^p = \{L_1^p, \ldots, L_N^p\}$, where $L_n^p$ is the emission delay to be applied to the transducer $114_n$, from the initial delays $E^0$ and, where applicable, complementary emission delays $E^1 \ldots E^p$ that will have been determined by the instructions 136 described below. In the embodiment described, the emission delays $L^p$ are determined by adding the initial delays $E^0$ and the complementary emission delays $E^1 \ldots E^p : L^p = E^0 + E^1 + \ldots + E^p$. At the first execution of instructions 124, that is to say when p is equal to zero, the emission delays $L^0$ are equal to the initial delays $E^0 : L^0 = E^0$. The initial delays $E^0$ are predefined in the computer program 122. They are for example zero delays (no delay between the transducers $114_1 \ldots 114_N$), in particular in the case where no information, even approximate, is known on the geometry of the object 102. In a variant, the initial delays $E^0$ may be non-zero, and generate for example a wave front partially adapted to the geometry of the object 102 as a first approximation. This variant is for example used in the case where the geometry of the object 102 is already at least partially known.

The computer program 122 also comprises instructions 126 designed to control the transducers $114_1 \ldots 114_N$ so that they emit to the object 102 ultrasonic waves having emission delays $L^p$ with respect to one another. To this end, the instructions 126 are designed to transmit control signals $C^p = \{C_1^p, \ldots, C_N^p\}$ to the transducers $114_1 \ldots 114_N$, where $C_n^p$ is the command transmitted to the transducer $114_n$ that is to have an emission delay $L_n^p$. These control signals $C^p$ are designed so that the transducers $114_1 \ldots 114_N$ each emit a pulse ultrasonic wave of pseudo time period T, the pulses being thus offset in time some with respect to the others of the emission delays $L^p$. The purpose of the emission delays $L^p$ is to compensate for the differences between the distances separating each transducer from the object 102 for the outward path so that the ultrasonic waves emitted by the transducers reach the object 102 at the same moment.

The computer program 122 also comprises instructions 128 designed to receive, from the transducers, measurement signals $S^p = \{S_1^p, \ldots, S_N^p\}$, where $S_n^p$ is the measurement signal supplied by the transducer $114_n$, measuring in particular the echoes due to the reflections of the ultrasonic waves on the object 102. The instructions 128 are also designed to record the measurement signals $S^p$. In the embodiment described, the instructions 128 are designed to record the measurement signal $S_n^p$ of each transducer $114_n$ on a time gate of predetermined duration and beginning for example when the control signal $C_n^p$ of this transducer $114_n$ is sent. The recordings of the measurement signals $S^p$ are denoted $EN^p = \{EN_1^p, \ldots, EN_N^p\}$, where $EN_n^p$ is the recording of the signal $S_n^p$ of the transducer $114_n$.

The computer program 122 also comprises instructions 130 designed to determine reception offsets $R^p = \{R_1^p, \ldots, R_N^p\}$ of the recordings $EN^p$, from the emission delays $L^p$, $R_n^p$ being the reception offset of the recording $EN_n^p$. In the embodiment described, the reception offsets $R^p$ are determined by means of the following formula: $R_n^p = \max(L_1^p, \ldots, L_N^p) - L_n^p$. The purpose of the reception offsets $R^p$ is to compensate for the differences between the distances separating each transducer from the object for the return path so that the echoes of the ultrasonic waves, which are assumed to be reflected at the same instant on the surface of the object 102 by virtue of the emission delays $L^p$, reach the transducers $114_1 \ldots 114_N$ at the same instant.

The computer program 122 also comprises instructions 132 designed to offset the recordings $EN^p$ of the measurement signals $S^p$ according to the reception offsets $R^p$. The recordings thus offset are denoted $\underline{EN}^p = \{\underline{EN}_1^p, \ldots, \underline{EN}_N^p\}$, where $\underline{EN}_n^p$ is the offset recording of the signal $S_n^p$ of the transducer $114_n$.

The computer program 122 also comprises instructions 134 designed to determine the round trip time $t^p = \{t_1^p, \ldots, t_N^p\}$, where $t_n^p$ is the round trip time determined from the offset recording $\underline{EN}_n^p$ corresponding to the transducer $114_n$. Thus the round trip times $t^p$ take account of the emission delays $L^p$ and the reception offsets $R^p$. In the embodiment described, the round trip time $t_n^p$ for each transducer $114_n$ is determined by detecting, for example, the maximum of the envelope of the corresponding signal $S_n^p$, recorded in the offset recording $\underline{EN}_n^p$.

The computer program 122 also comprises instructions 136 designed to determine new complementary emission delays $E^{p+1}$ from the round trip times $t^p$. In the embodiment described, the complementary emission delays $E^{p+1}$ are determined by means of the following formula: $E_n^{p+1} = \frac{1}{2}[\max(t_1^p, \ldots, t_N^p) - t_n^p]$.

The computer program 122 also comprises instructions 138 designed to evaluate a stop test in order to determine stoppage if the stop test is satisfied or continuation of the execution of the computer program 122 in the contrary case. In the latter case, the instructions 138 are designed to return to the instructions 124 in order to cause a new iteration of the instruction loop 124 to 138, with the new complementary emission delays $E^{p+1}$, so that the set of complementary emission delays comprises the p+1 complementary emission delays $E^1, \ldots, E^{p+1}$. In the present description, it is at this moment that the index p is incremented by one unit, so that the set of complementary emission delays is at this moment denoted $E^1, \ldots, E^p$, in accordance with the description of the instructions 124. In the embodiment described, the stop test consists of checking that the following inequality is satisfied:

$$\max(E_1^p, \ldots, E_N^p) \le \frac{T}{4},$$

where T is the pseudo time period of the ultrasonic waves emitted by the transducers and where $E^p$ are the last complementary emission delays determined at step 134 (where they were denoted $E^{p+1}$). In a variant, the instructions 138 can be designed to stop the execution of the program 122 at the end of a predetermined number of executions of the loop, for example four or five, that is to say p equal to three or four.

With reference to FIG. 2, an inspection method 200 implemented by the device 100 of FIG. 1 will now be described.

During a step 202, the processing unit 118 executing the instructions 124 determines the emission delays $L^p = \{L_1^p, \ldots, L_N^p\}$ from the initial delays $E^0$ and, where applicable, the complementary emission delays $E^1 \ldots E^p$ that will have been determined at step 222 described below.

During steps $204_1$ to $204_N$, the processing unit 118 executing the instructions 126 controls each transducer $114_n$ so that it sends ultrasonic waves to the object 102, the ultrasonic waves emitted by the transducers $114_1 \ldots 114_N$ having the emission delays If with respect to one another. To this end, the processing unit 118 executing the instructions 126 transmits each command signal $C_n^p$ to the corresponding transducer $114_n$, the command signals $C^p$ having the emission delays $L^p$ with respect to one another.

During steps $206_1$ to $206_N$, the processing unit 118 executing the instructions 128 begins, following the transmission of each command signal $C_n^p$ to the corresponding transducer $114_n$, the recording of the measurement signal $S_n^p$ supplied by the transducer $114_n$.

During steps $208_1$ to $208_N$, each transducer $114_1 \ldots 114_N$ sends, following the reception of its command signal, a pulse ultrasonic wave of pseudo time period T. Thus the pulses are offset in time with respect to one another from the emission delays $L^p$.

During steps $210_1$ to $210_N$, each transducer $114_n$ receives the echoes of the ultrasonic waves reflected on and in the object 102.

During steps $212_1$ to $212_N$, each transducer $114_n$ supplies its measurement signal $S_n^p$, measuring in particular the echoes of the ultrasonic waves on the surface of the object 102. The processing unit 118 executing the instructions 128 receives this signal $S_n^p$ and records it in the recording $EN_n^p$.

During steps $214_1$ to $214_N$, the processing unit 118 executing the instructions 128 stops the recording $EN_n^p$ of the signal $S_n^p$ of the transducer $114_n$.

During a step 216, the processing unit 118 executing the instructions 130 determines the reception offsets $R^p$ from the emission delays $L^p$.

During a step 218 the processing unit 118 executing the instructions 132 offsets the recordings $EN^p$ of the measurement signals $S^p$ according to the reception offsets $R^p$, in order to obtain the offset recordings $\underline{EN}^p$.

During a step 220, the processing unit 118 executing the instructions 134 determines the round trip times $t^p = \{t_1^p, \ldots, t_N^p\}$ between the transducers $114_1 \ldots 114_N$ and the object 102 taking account of the emission delays $L^p$ and the reception offsets $R^p$, from the offset recordings $\underline{EN}^p$.

During a step 222, the processing unit 118 executing the instructions 136 determines new complementary emission delays $E^{p+1}$ from the round trip times $t^p$.

Thus it will be noted that steps 216 to 222 make it possible to determine complementary emission delays $E^{p+1}$ from the measurement signals $S^p$.

During a step 224, the processing unit 118 executing the instructions 138 determines the stoppage or continuation of the execution of the computer program 122 and, in the latter case, increments p by one unit before returning to step 202.

The method of FIG. 2 is implemented at each position of the movement of the probe 106 with respect to the object 102. In the case where the object has small variations in geometry along this movement, the initial emission delays $E^0$ at a given position are advantageously taken to be equal to the last emission delays $L^p$ determined at a previous position, in particular the directly previous position. This makes it possible to increase the speeds of inspection of parts with very extensive surfaces by reducing the number of firings at each position.

With reference to FIGS. 3 to 9, an example of implementation of the inspection method of FIG. 2 will be detailed.

With reference to FIG. 3, in the example described, the object 102 is a part having an elbow 302 with a high angle and therefore a small radius of curvature, which the probe 106 of the inspection device 100 is intended to inspect. The probe 106 comprises for example N=49 transducers.

In order to inspect the elbow 302, the method of FIG. 2 is implemented.

At a first execution of the loop of steps, that is to say when p is equal to zero (first iteration), ultrasonic waves are emitted at steps $208_1$ to $208_N$ by the transducers with emission delays $L^0$ equal to the initial delays $E^0$: $L^0 = E^0$, zero in the example described.

Offset recordings $\underline{EN}^p$ are then obtained at step 218, including those of the first, $24^{th}$ and $49^{th}$ transducers, which are shown in FIG. 4.

With reference to FIG. 5, the amplitude of the envelope of the offset signals $\underline{EN}^p$ is determined at step 220. They are shown in FIG. 5, in which the vertical axis corresponds to time, the horizontal axis to the transducers and the amplitude of the envelope to the grey level of the points. This representation is known, as indicated previously, as "B-scan". According to a known representation of B-scan, the round trip distance $t_n^0$ for each transducer $114_n$ is determined as being the distance separating the origin of the maximum times from the envelope amplitude, that is to say from the darkest point on the vertical line corresponding to the transducer $114_n$. Moreover, the appearance of a dark line LF will be noted, grouping together the darkest points on each vertical line and corresponding to the surface echo of the elbow 302, followed by a high structure noise BF under no circumstances making it possible to reveal the presence of any defect in the object 102.

In a variant, it would be noted that the B-scan representation may be modified by applying a moving average treatment to the measurement signals recorded in the offset recordings $\underline{EN}^p$.

The complementary emission delays $E^1$ are then determined at step 222, and the continuation of the execution of the program is decided at step 224 so that a first repetition (second iteration) of the steps is performed (p is incremented to 1).

FIG. 6 shows the B-scan obtained at step 220 of this first repetition (or second iteration), from the emission delays $L^1 = E^0 + E^1$. The complementary emission delays having been calculated from the round trip times, it will be expected to obtain a horizontal dark line that would indicate that the ultrasonic waves of all the transducers reach the elbow 302 at the same instant. However, it will be noted that this is not the case and that the dark line LF, corresponding to the surface of the elbow 302, is still a little curved.

With reference to FIG. 7, the inventors have determined that, for very complex parts, the first iteration and its repetition up to step 220 do not suffice to correct the differences in geometry and phenomena of superimposition of waves on the same measurement signal that result therefrom. This is because each transducer detects an echo that is the product of the interference between the echo resulting from its own emission of ultrasonic waves and the echoes resulting from the ultrasonic waves emitted by the adjoining transducers. The inventors nevertheless determined that it is possible to adapt the inspection apparatus 100 to very complex geometries, such as the elbow 302, by iterating the steps of the method 200 of FIG. 2 several times completely.

Thus, FIG. 8 shows the B-scan obtained at step 220 of the second repetition (or third iteration), from the emission delays $L^2 = E^0 + E^1 + E^2$, while FIG. 9 shows the B-scan obtained at step 220 of the third repetition (or fourth iteration), from the emission delays $L^3 = E^0 + E^1 + E^2 + E^3$. It will be noted that the dark line LF is practically horizontal on this last figure, indicating that the inspection apparatus 100 is suited to the geometry of the object 102, that is to say that the ultrasonic wave front formed by all the waves generated by all the transducers $114_1 \ldots 114_N$ has the same curvature as the surface of the elbow 302.

In addition, the internal noise has disappeared, revealing the actual structure of the object 102, in particular a light line LC indicating the bottom of the elbow 302. Thus, any defect in the object 102 becomes apparent by virtue of a multiple repetition of the loop of steps previously described. In particular, defects of the delamination type, which are generally situated close to the bottom LC, are better detected.

It will be noted moreover that the invention is not limited to the embodiment described previously. It will be clear in fact to a person skilled in the art that various modifications can be made to the embodiment described above, in the light of the teaching that has just been disclosed to him.

In particular, the computer program instructions could be replaced by electronic circuits dedicated to the functions performed during the execution of these instructions.

In addition, the method according to the invention can be implemented with a mechanical movement of the probe or by proceeding with an electronic movement of a sub-opening along the total opening of the sensor where the transducers are situated.

In the following claims, the terms used must not be interpreted as limiting the claims to the embodiment disclosed in the present description, but must be interpreted in order to include therein all equivalents that the claims cover because of their formulation and the provision of which is within the capability of a person skilled in the art applying his general knowledge to the implementation of the teaching that has just been disclosed to him.

The invention claimed is:

1. A method for controlling ultrasonic transducers of an ultrasonic probe for inspecting an object, comprising:
   controlling the transducers so they emit towards the object ultrasound waves having initial emission delays $E^0$ with respect to one another;
   receiving from the transducers measurement signals $S^0$, measuring echoes due to reflections of the ultrasound waves on the object;
   determining complementary emission delays $E^1$ from the measurement signals $S^0$; and
   controlling the transducers so they emit towards the object ultrasound waves having emission delays $L^1$ with respect to one another, the emission delays $L^1$ having been determined from the initial emission delays $E^0$ and the complementary emission delays $E^1$;
   further comprising, iterated at least once, with the iteration number being denoted p:
   receiving from the transducers new measurement signals $S^p$, measuring echoes due to reflections of the ultrasound waves on the object, the ultrasound waves having emission delays $L^p$ with respect to one another, the emission delays $L^p$ having been determined from the initial emission delays $E^0$ and all the complementary emission delays $E^1 \ldots E^p$ determined previously;
   determining new complementary emission delays $E^{p+1}$ from the new measurement signals $S^p$; and
   controlling the transducers so they emit ultrasound waves towards the object, the ultrasound waves having emission delays $L^{p+1}$ with respect to one another, the emission delays $L^{p+1}$ having been determined from the initial emission delays $E^0$ and all the complementary emission delays $E^1 \ldots E^{p+1}$ determined previously.

2. A method according to claim 1, wherein, during the new complementary emission delays $E^{p+1}$ being determined from the new measurement signals $S^p$, further comprising:
   determining round trip times $t^p$ from the new measurement signals $S^p$; and
   determining the new complementary emission delays $E^{p+1}$ from the trip times $t^p$.

3. A method according to claim 2, wherein, during the round trip times $t^p$ being determined from the new measurement signals $S^p$, further comprising, for each transducer:
   determining a reference instant on the new measurement signal $S_n^p$ supplied by the transducer in question, for an instant where an envelope of amplitude of the new measurement signal $S_n^p$ takes a maximum value, n designating the index of the transducer in question.

4. A method according to claim 2, wherein, during the round trip times $t^p$ being determined from the new measurement signals $S^p$, further comprising:
   determining reception offsets $R^p$ from the emission delays $L^p$; and
   offsetting in time the new measurement signals $S^p$ according to the reception offsets $R^p$.

5. A method according to claim 2, wherein, during the new complementary emission delays $E^{p+1}$ being determined from the trip times $t^p$ further comprising, for each transducer:
   determining the new complementary emission delay $E_n^{p+1}$ for the transducer in question according to equation:
   $E_n^{p+1} = \frac{1}{2}[\max(t_1^p, \ldots, t_N^p) - t_n^p]$, in which $t_n^p$ is round trip time determined from the new measurement signal $S_n^p$ supplied by the transducer in question, n designating the index of the transducer in question and N the number of transducers.

6. A method according to claim 1, further comprising:
   at an end of each iteration p, evaluating a stop test which, if it is satisfied, stops the method, and which, if it is not satisfied, causes the execution of a new iteration p+1.

7. A method according to claim 6, wherein the ultrasound waves emitted by the transducers are pulse waves having a pseudo time period T, and wherein the stop test comprises verification of the following inequality:

$$\max(E_1^p, \ldots, E_N^p) \leq \frac{T}{4}.$$

8. A method according to claim 6, wherein the stop test comprises a check that the number of iterations has reached a predetermined number, or reached three or four iterations.

9. A non-transitory computer readable medium including computer executable instructions for execution of an inspection method according to claim 1, when the instructions are executed on a computer.

10. An ultrasonic inspection device for inspecting an object comprising:
    a probe comprising a housing and ultrasonic transducers attached to the housing; and
    a controller configured to perform a method that includes:
    controlling the transducers so they emit towards the object ultrasound waves having initial emission delays $E^0$ with respect to one another;
    receiving from the transducers measurement signals $S^0$, measuring echoes due to reflections of the ultrasound waves on the object;
    determining complementary emission delays $E^1$ from the measurement signals $S^0$; and
    controlling the transducers so they emit towards the object ultrasound waves having emission delays $L^1$ with respect to one another, the emission delays $L^1$ having been determined from the initial emission delays $E^0$ and the complementary emission delays $E^1$;
    the method further including, iterated at least once, with the iteration number being denoted p:
    receiving from the transducers new measurement signals $S^p$, measuring echoes due to reflections of the ultrasound waves on the object, the ultrasound waves having emission delays $L^p$ with respect to one another, the emission delays $L^p$ having been determined from the initial emission delays $E^0$ and all the complementary emission delays $E^1 \ldots E^p$ determined previously;
    determining new complementary emission delays $E^{p+1}$ from the new measurement signals $S^p$; and
    controlling the transducers so they emit ultrasound waves towards the object, the ultrasound waves having emission delays $L^{p+1}$ with respect to one another, the emission delays $L^{p+1}$ having been determined from the initial emission delays $E^0$ and all the complementary emission delays $E^1 \ldots E^{p+1}$ determined previously.

* * * * *